US00PP35027P2

(12) United States Plant Patent
Navarro

(10) Patent No.: US PP35,027 P2
(45) Date of Patent: Mar. 14, 2023

(54) APPLE TREE NAMED 'SPINK754'

(50) Latin Name: ***Malus domestica* Borkh.**
Varietal Denomination: SPINK754

(71) Applicant: IVU California, LLC, Brentwood, CA (US)

(72) Inventor: Alejandro Navarro, Curico (CL)

(73) Assignee: IVU California, LLC, Brentwood, CA (US)

( * ) Notice: Subject to any disclaimer, the term of this patent is extended or adjusted under 35 U.S.C. 154(b) by 0 days.

(21) Appl. No.: 17/579,709

(22) Filed: Jan. 20, 2022

(51) Int. Cl.
*A01H 5/08* (2018.01)
*A01H 6/74* (2018.01)

(52) U.S. Cl.
USPC ..... Plt./161

(58) Field of Classification Search
USPC ..... Plt./161
See application file for complete search history.

(56) References Cited

PUBLICATIONS

Plant Patent Application publication US 2019/0323562.*

* cited by examiner

*Primary Examiner* — Annette H Para
(74) *Attorney, Agent, or Firm* — R. Scott Kimsey, Esq.

(57) ABSTRACT

A new and distinct variety of apple tree is described and denominated SPINK754. The new variety exhibits an attractive and intense color, harvesting 1 to 2 weeks prior to the standard variety, and strong post-harvest preservation when grown under the conditions prevailing in the central valley of Chile.

10 Drawing Sheets

Latin name: *Malus domestica* Borkh.
Variety denomination: SPINK754.

RELATED APPLICATIONS

Not Applicable.

STATEMENT REGARDING FEDERALLY SPONSORED RESEARCH OR DEVELOPMENT

Not Applicable.

ORIGIN AND ASEXUAL REPRODUCTION

The present disclosure relates to a new and distinct variety of apple tree, *Malus domestica*, that has been denominated SPINK754, and more specifically to an apple tree variety that is principally characterized by an attractive and intense color, harvesting one to two weeks prior to the 'Cripps Pink' variety (unpatented), and presents longer post-harvest preservation at its orchards of origin in the central valley of Chile. Attractive color and good handling and storage characteristics are well known to be important commercial factors when it comes to apples or other fruits. The new variety is further characterized by greater, more uniform starch content than 'Cripps Pink', and longer resistance to internal browning post-harvest.

In March, 2008, a mutation of a branch of a 'Cripps Pink' tree (unpatented) was selected on rootstock 'MM106' (unpatented) in a 20 hectare orchard located in the Curicó valley, central zone of Chile, located at 35 latitude south. The normal harvest date of 'Cripps Pink' at this geographic location is one to two weeks later than the selected mutation. The mutation presented an intense pink coloration covering approximately 80% of the fruit, a greater degree of coloration than the approximately 60% coverage found on other fruit in the orchard.

In 2009 a total of ten trees of the new variety were propagated asexually in the central valley of Chile by grafting onto 'M9 T337' (unpatented). The first fruits were obtained in 2011. The new variety was evaluated for stability through successive generations from 2011 to 2021 and determined to be stable. It was also determined that the new variety presents a longer post-harvest life in the central valley of Chile, where the 'Cripps Pink' variety exhibits high internal browning damage to the fruit after harvest. Fruits of the new variety either lacked this problem entirely or presented the problem to a very small degree.

SUMMARY OF THE INVENTION

The SPINK 754 apple tree is characterized by an attractive and intense color, an earlier harvesting time than the 'Cripps Pink' variety, and a strong diminishment in internal browning of fruit stored for more than five months. The fruit is ripe for harvesting and shipment during approximately mid-April under conditions prevailing in the central valley of Chile. SPINK 754 is distinguished from its 'Cripps Pink' parent and similar cultivars primarily by a harvesting date of from one to two weeks earlier than 'Cripps Pink' and the aforementioned long post-harvest preservation in storage.

BRIEF DESCRIPTION OF THE ILLUSTRATIONS

The accompanying photographs consist of color photographs as follows.

DETAILED DESCRIPTION OF THE INVENTION

Figure 1:
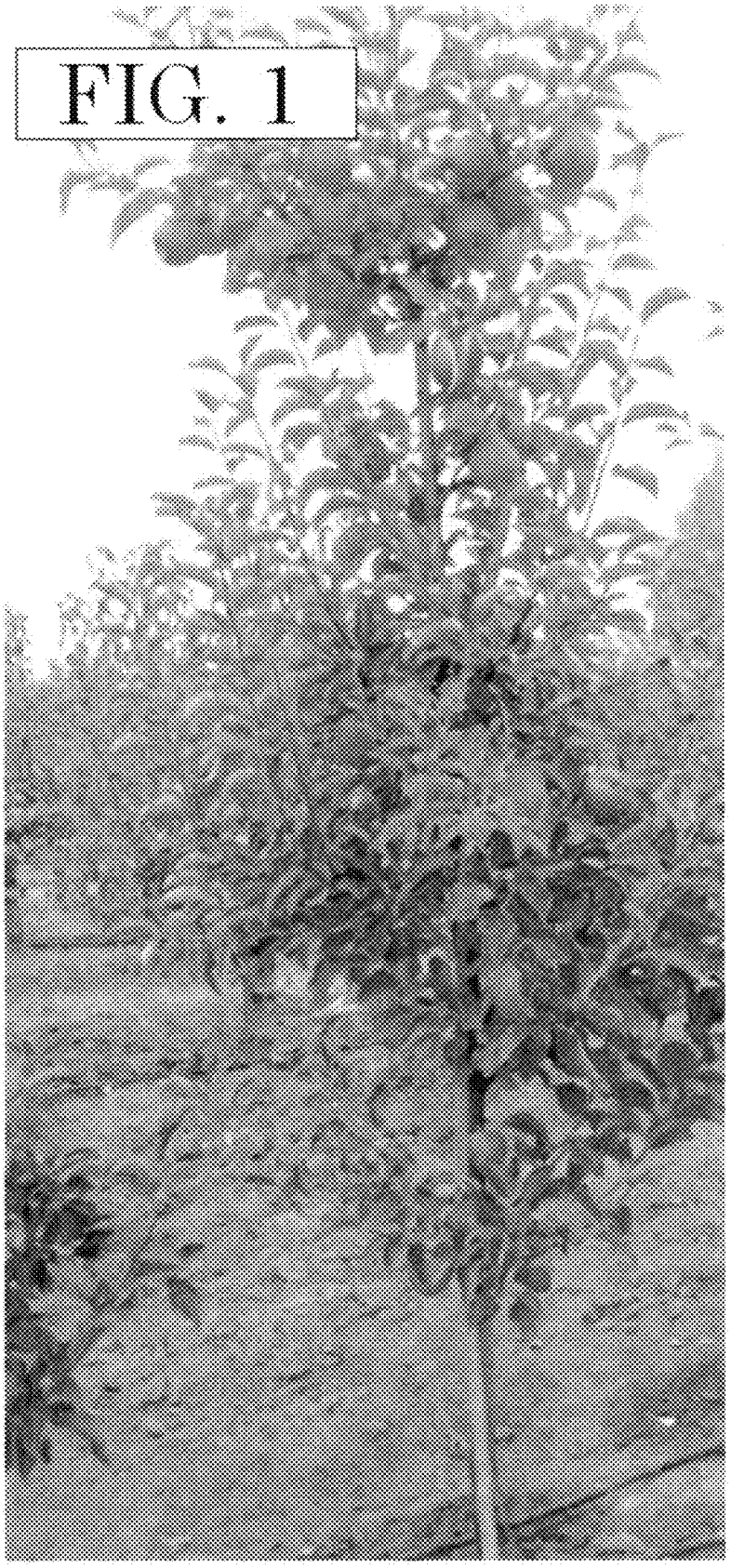
FIG. 1 depicts a 3rd generation tree of the new variety, approximately five years old, growing on or about Apr. 5, 2014 in the central valley of Chile
Figure 2:
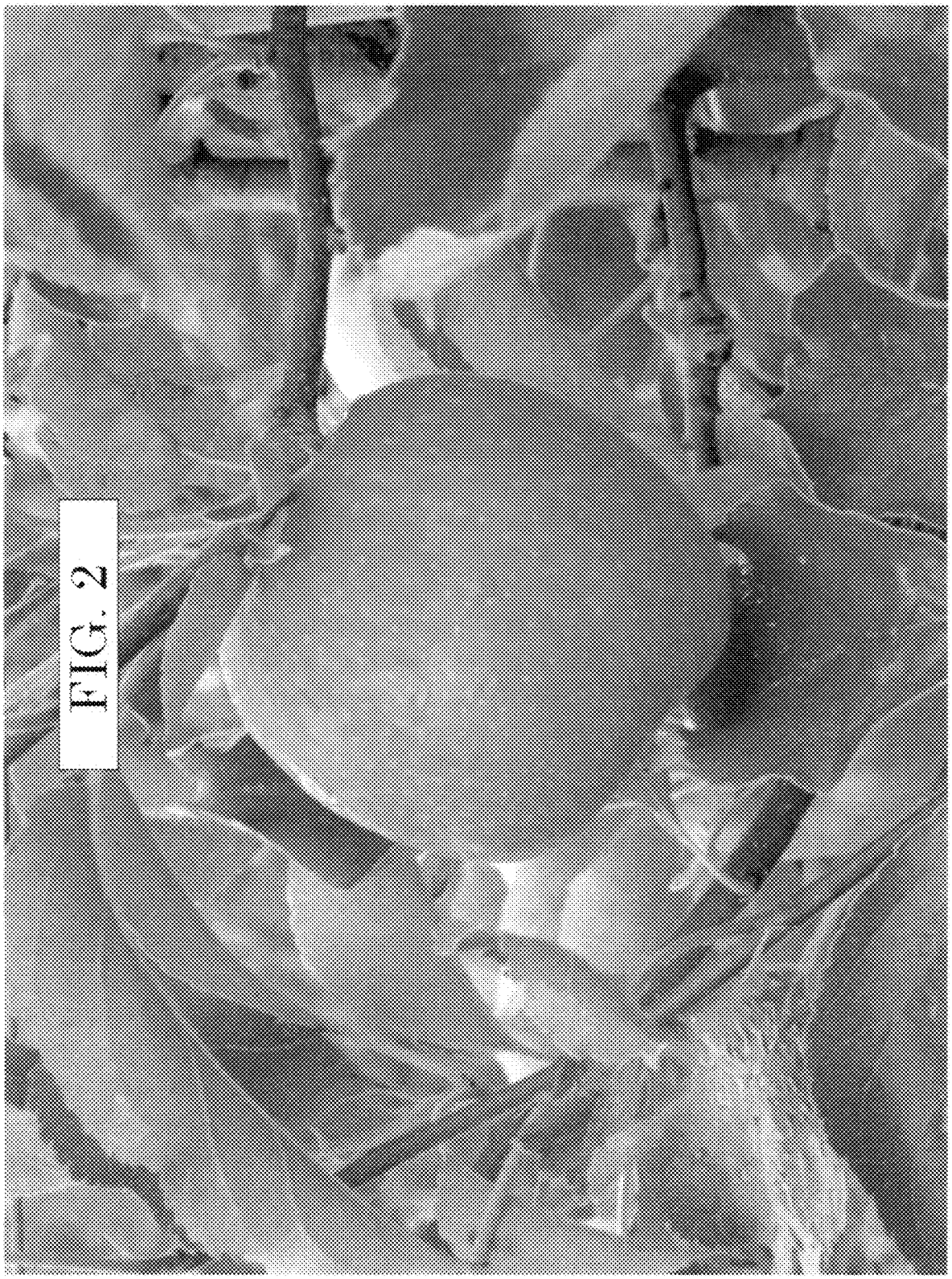
FIG. 2 is a close view of the fruit of the new variety, growing on or about Apr. 5, 2014 in the central valley of Chile.
Figure 3:
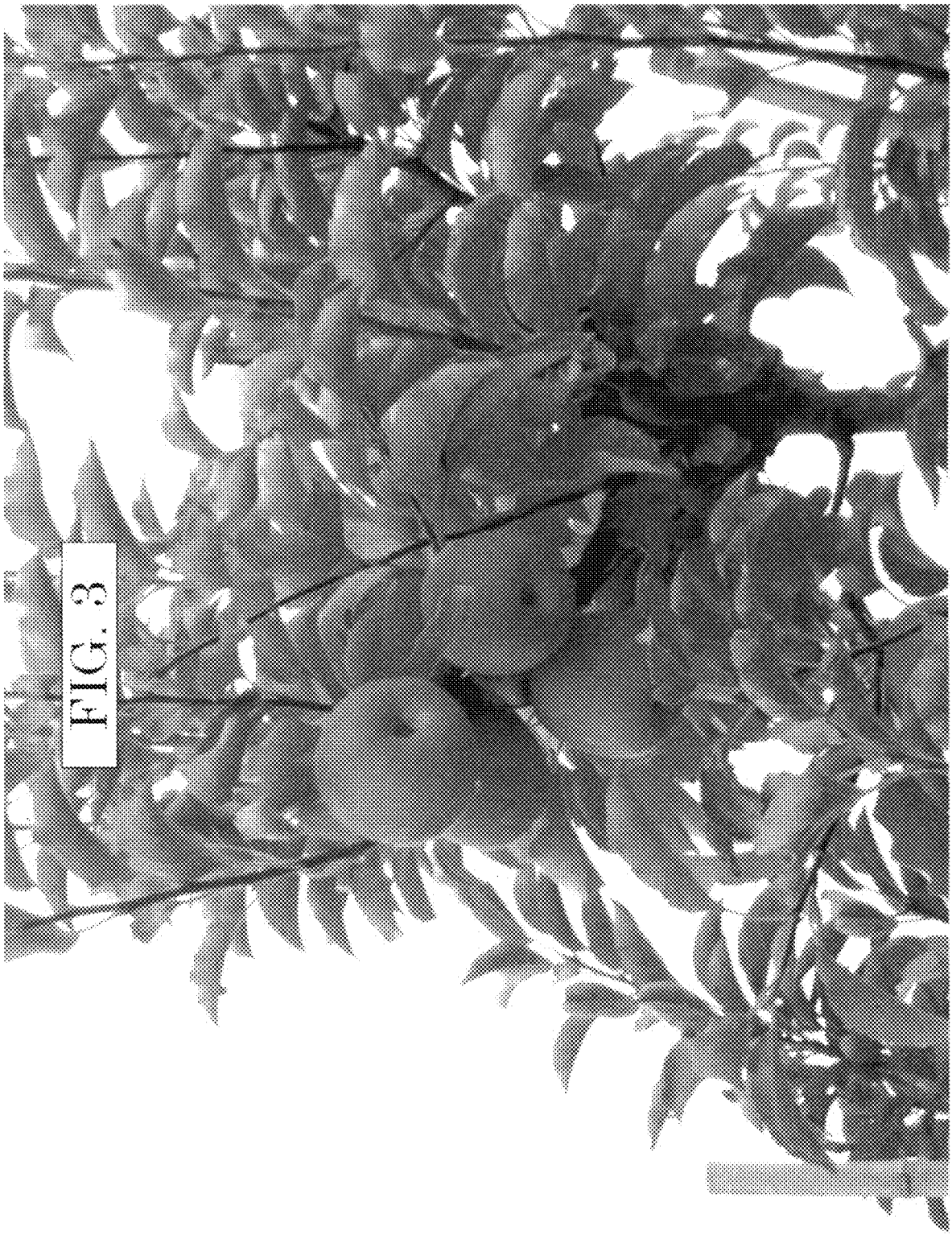
FIG. 3 is a cluster of fruit from a 3rd generation tree of the new variety, approximately five years old, growing on or about Apr. 5, 2014, in the central valley of Chile.
Figure 4:
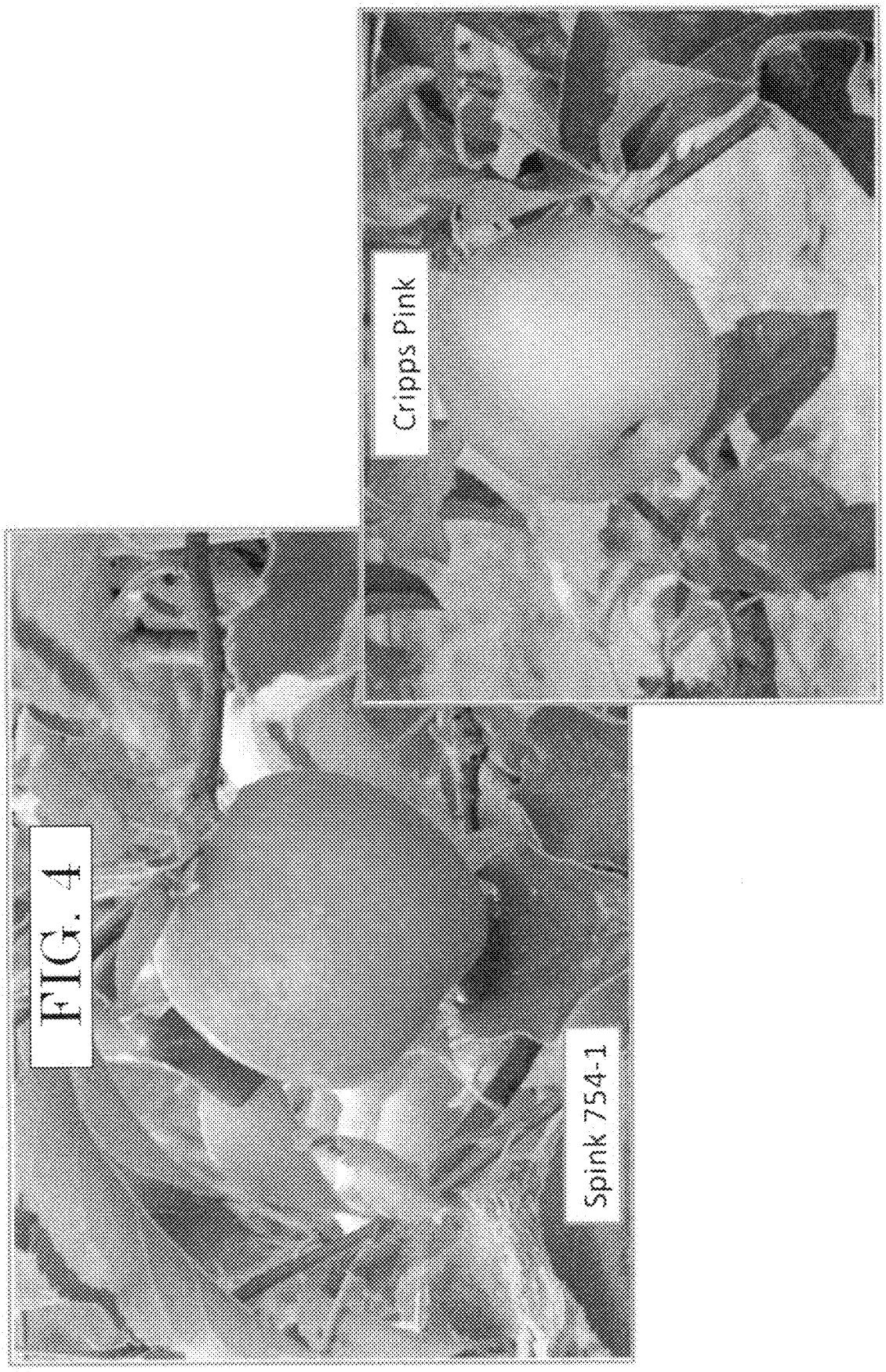
FIG. 4 is a comparison of the fruit of the new variety, and that of Cripps Pink, both growing on or about Apr. 5, 2014 in the central valley of Chile.
Figure 5:
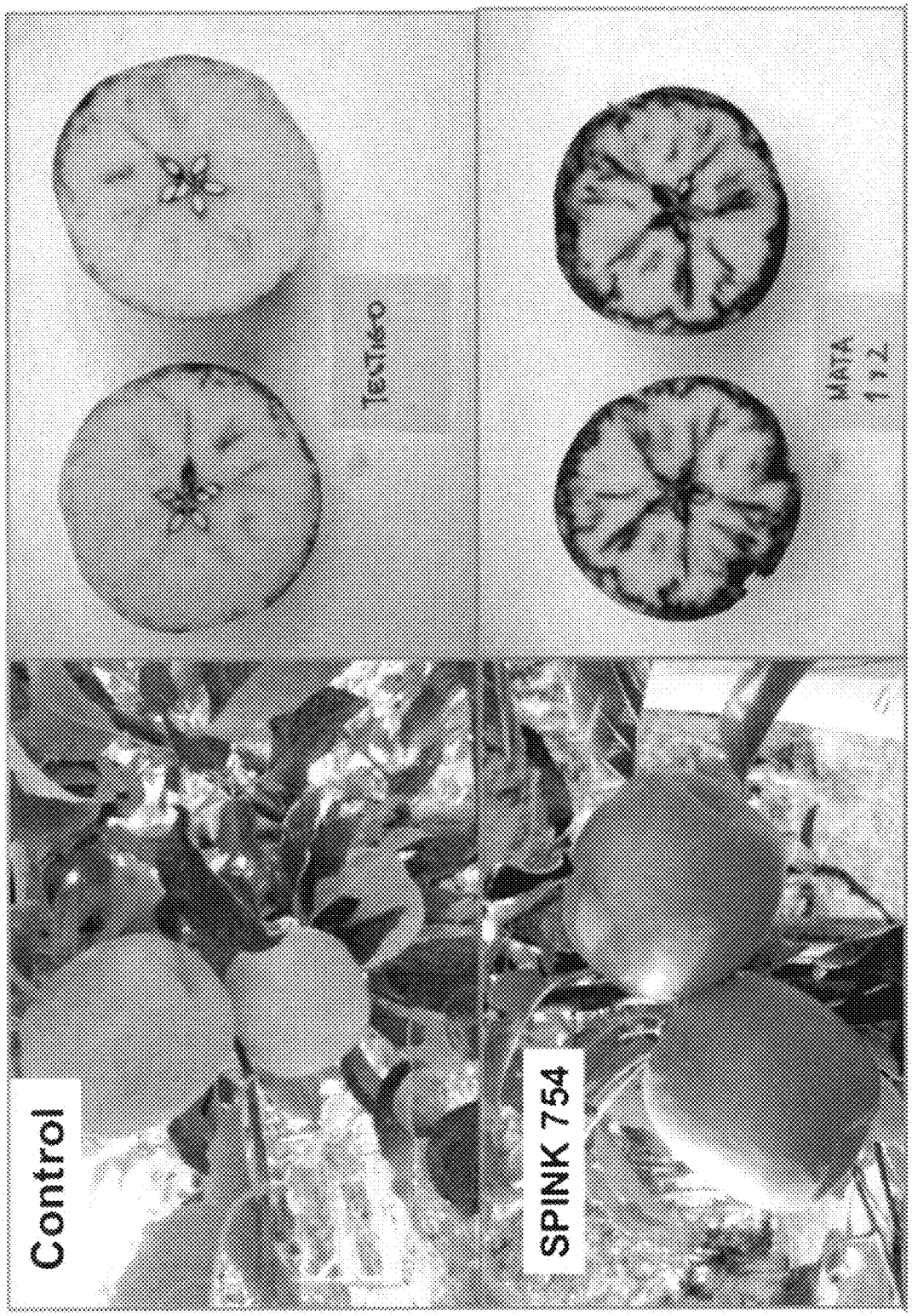
FIG. 5 is a comparison of the starch content of a 'Cripps Pink' control and the fruit of the new variety, both grown in 2011 in the central valley of Chile.
Figure 6:
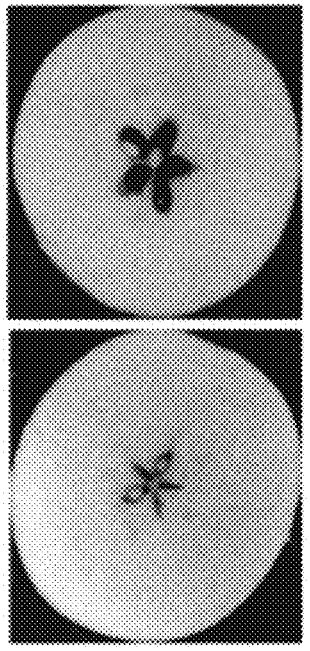
FIG. 6 is a comparison of internal browning of the new variety and that of the 'Cripps Pink' and 'Rosy Glow' (unpatented) varieties, with each fruit shown after about 150 days of cold storage.
Figure 6:
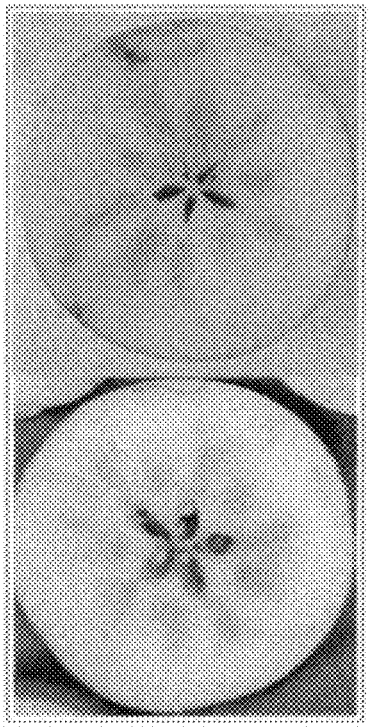
Figure 7:
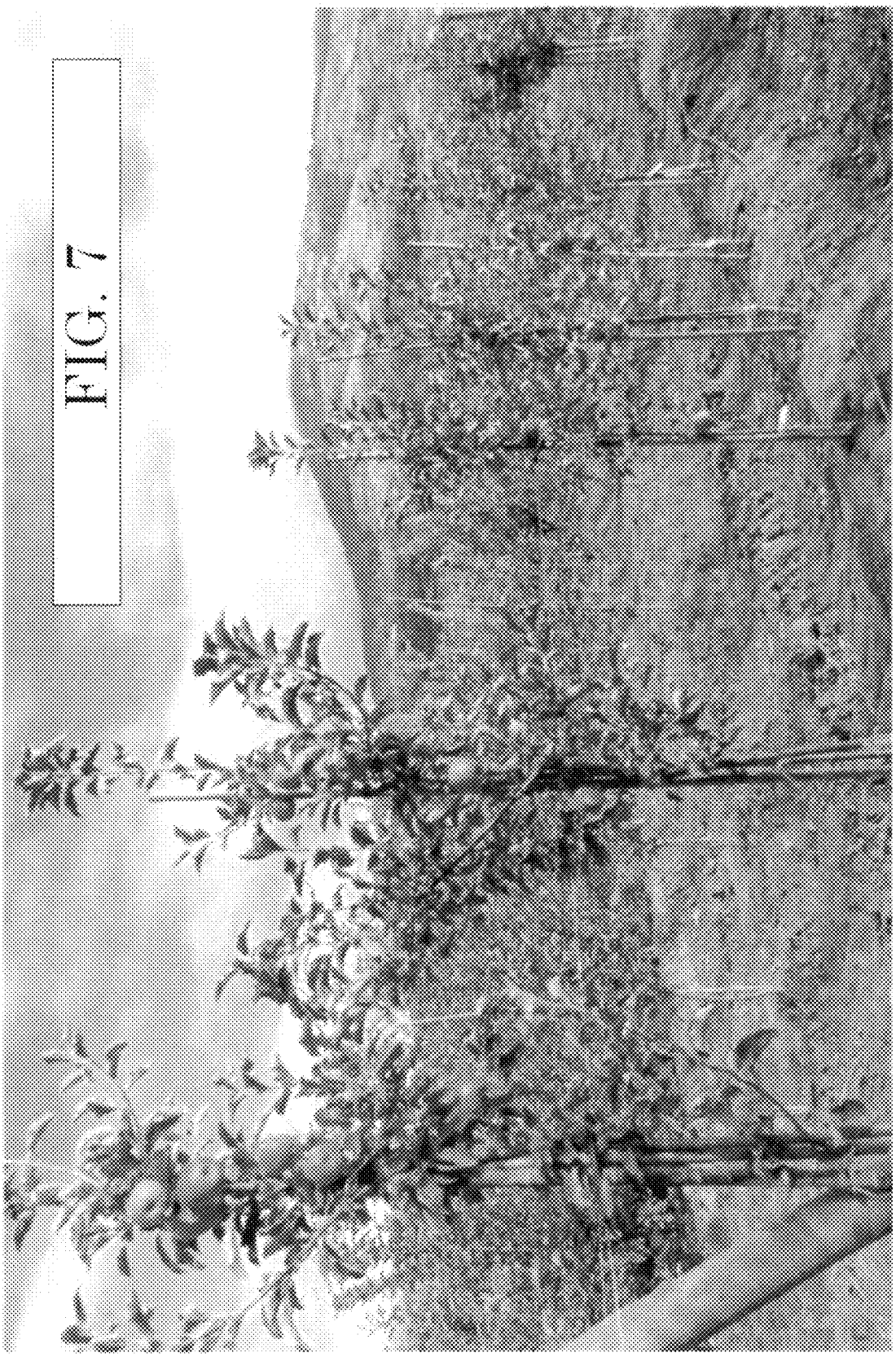
FIG. 7 is an early third generation tree of the new variety, approximately two years old, showing its first fruit on or about Apr. 15, 2011.
Figure 8:
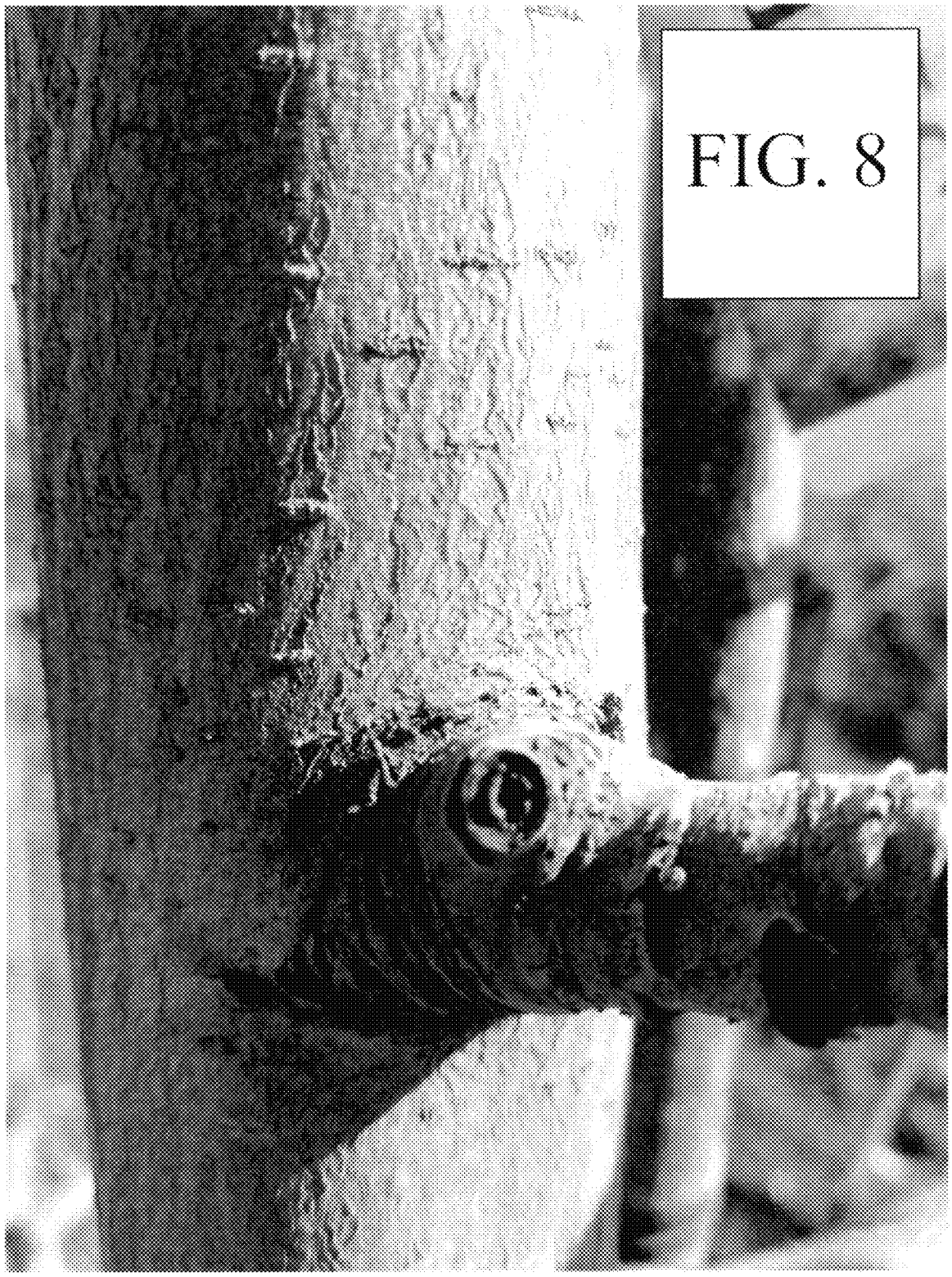
FIG. 8 is a close view of a stem and branch of a tree of the new variety growing in the central valley of Chile.
Figure 9:
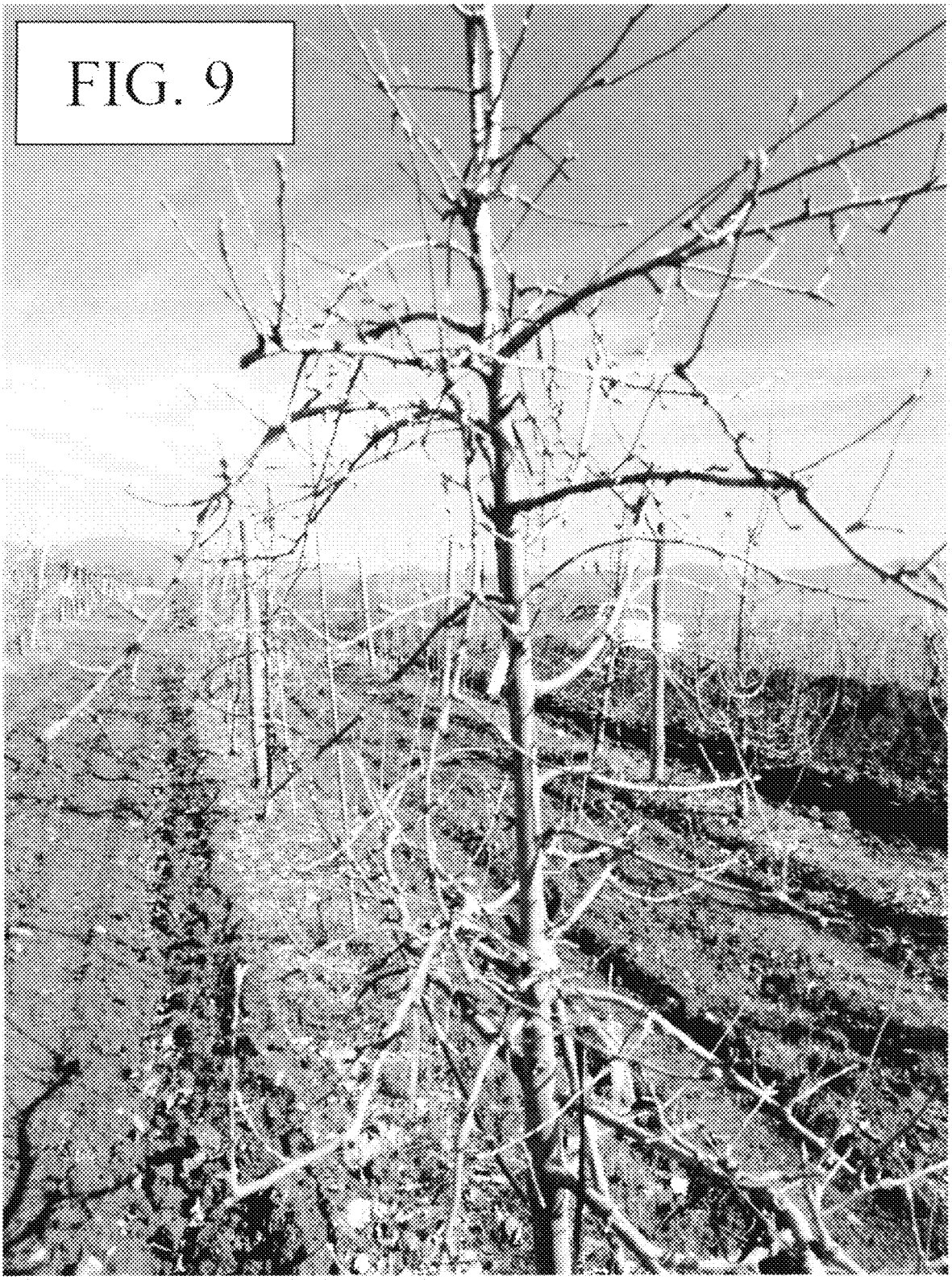
FIG. 9 is a full view of a 3rd generation tree of the new variety, approximately five years of age, prior to refoliation, in the central valley of Chile.
Figure 10:
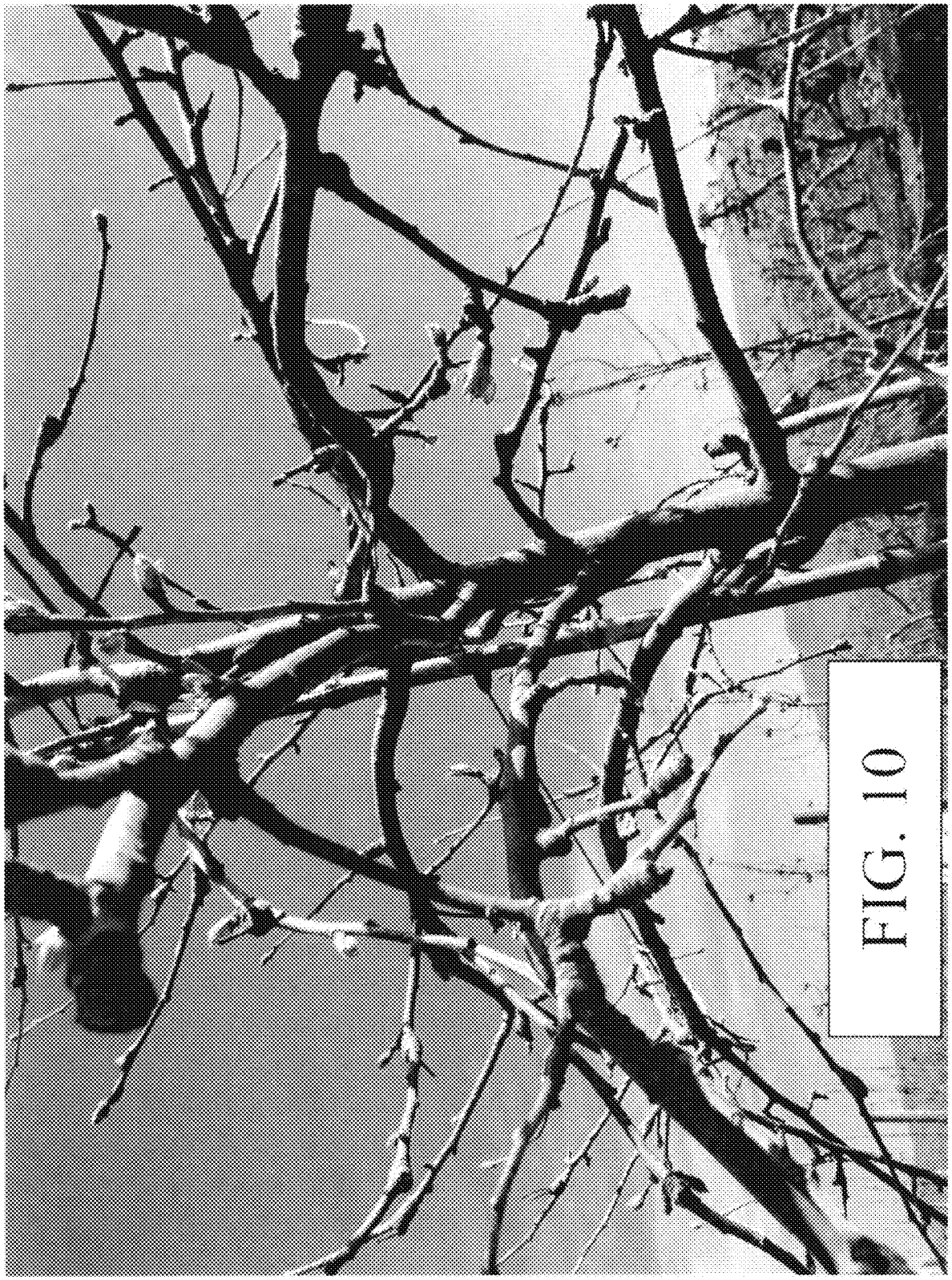
FIG. 10 is a close view of branches and budding of a 3rd generation tree of the new variety, approximately five years of age, growing in the central valley of Chile.

Referring to the botanical description of the new and distinct variety, the following traits and characteristics have been observed in representative plants of the new variety observed in their third and fourth years of growth and grown under production conditions in the central valley of Chile.

BOTANICAL DESCRIPTION

Color codes are taken from The Colour Chart of The Royal Horticultural Society.

Tree:

- *Type*.—Ramified; extended habit.
- *Vigor*.—Medium to strong.
- *Fruiting*.—Only in long stalks.
- *Branching*.—Branches born from the trunk almost at right angles at the portions proximal to the trunk, curving upwards at the distal end.
- *Density*.—Very dense with a large number of twigs.
- *Growing season*.—Start of budding in late winter, growing until mid-autumn.
- *Hardiness*.—Presents resistance to commonly-occurring diseases in the Central Valley of Chile.

Trunk characteristics:

- *Diameter*.—2.5 inches.
- *Surface texture*.—Smooth with stretch marks.
- *Color of bark*.—116 A (Fan 4) with sun exposure; 199 A (Fan 4) on the shaded side.
- *Lenticels*.—A large number of elongated lenticels disposes perpendicularly.

Branch characteristics:

- *Size*.—0.5 to 1 inch in diameter (with thicker basal branches).
- *Surface texture*.—Smooth texture without presentation of large stretch marks.
- *Crotch angle*.—Branch insertion in the trunk is at almost ninety degrees.
- *Internode length*.—Medium length after one year, observed in middle third of branch.
- *Color*.—152 A (Fan 4) in the shade; 164 A (Fan 4) in the sun.
- *Pubescence*.—Medium, after one year.
- *Number of lenticels*.—Large number of circular-shaped lenticels of color 162 A (Fan 4), with a diameter of approximately 0.5 to 1 mm with a variable distribution of lenticels per $cm^2$ (1 to 5).
- *Fruiting branches*.—Occurring over 80 cm from the graft with an approximate diameter of 4 mm and an angle of insertion in the branch of approximately forty-five degrees.

Leaves:

- *Leaf base*.—Horizontal.
- *Length*.—110.95 mm (average).
- *Width*.—66.16 mm (average).
- *Color*.—Dark green (136 B (Fan 3) upper side; 137 C (Fan 3) underside).
- *Incisions on edge*.—Bicrenate.
- *Pubescence on bottom surface*.—Absent or weak.
- *Petiole length*.—35.88 mm.
- *Petiole thickness*.—1.748 mm.
- *Petiole color*.—Medium green with poor Antocian coloring (191 B (Fan 4)).
- *Nectaries*.—Not Present.

Flowers:

- *Flower diameter*.—53.473 mm (average).
- *Fragrance*.—Not detected.
- *Flowers per panicle*.—6 flowers (average).
- *Size of flower buds*.—9.836 mm (average).
- *Shape of flower buds*.—Oval.
- *Color of flower buds*.—Dark Pink (157 C (Fan 2)).
- *Petal disposition*.—Intermediate.
- *Date of full bloom*.—3rd week of September in the Central Valley of Chile.
- *Duration of bloom*.—Approximately fifteen days.
- *Petal margin*.—Smooth.
- *Petal texture*.—Corrugated.
- *Color of petals*.—Beam: White with light pink edges (155 C (Fan 4)); Underside: White with irregular light pink spots (115 D (Fan 4)); WS 154.
- *Stamen size*.—9.29 mm average length; 2.1 mm average width.
- *Stamen color*.—White (155 C (Fan 4)).
- *Stamen (anther) color*.—Yellow (162 B (Fan 4)).
- *Pollen*.—Colorless.
- *Stigma, style, ovary color*.—Green (151 C (Fan 4)).
- *Stigma, style, ovary length*.—11.78 mm.
- *Length of peduncle*.—14.855 mm (average).
- *Peduncle caliper*.—2.831 mm diameter (average).
- *Peduncle color*.—Medium green (151 B (Fan 3)).
- *Position of stigma in relation to anthers*.—At the same level.
- *Good pollinator*.—Granny Smith.

Fruit:

- *Date of first picking*.—Iodine test indicates harvest period starts 10 to 15 days before 'Cripps Pink' (1st week of April) in the Central Valley of Chile; Coverage of more than 80% of upper color (179 A (Fan 4)).

*Date of last picking.*—2nd week of April in the Central Valley of Chile.
*Extension of coloring of anthocyanin in young fruit.*—Medium.
*Size.*—80.447 mm length (average); 77.051 mm width/diameter (average).
*Shape.*—Cylindrical, generally.
*Weight.*—237.727 g (average).
*Surface color.*—Red Pink (179A (Fan 4)).
*Ribbing.*—Moderate.
*Crown at the end of the cup.*—Moderate.
*Bloom of epidermis.*—Strong.
*Greasiness of epidermis.*—Strong.
*Distribution of top color.*—Uniform.
*Zone of russeting around peduncular base.*—Absent or small.
*Zone of russeting on face.*—Absent or small.
*Zone of russeting of eye cavity.*—Absent or small.
*Firmness of pulp.*—Very firm.
*Color of pulp.*—Cream (158 B (Fan 4)).
*Opening of loculus.*—Closed or slightly open.
*Start time of flowering.*—Very late.
*Length of stem.*—14.855 mm (average).
*Stem caliper.*—2.831 mm diameter (average).
*Stem color.*—Medium green (151 B (Fan 3)).
*Keeping quality.*—Thirty days after harvest unrefrigerated; up to six months cold storage life.
*Eating quality/taste.*—Good eating quality; firm flesh with good juice production; sweet flavor with subtle acid.
*Aroma.*—Highly aromatic; complex bouquet.

The new variety exhibits the characteristics shown and described when grown under the ecological conditions prevailing in the central valley of Chile. It is understood that variations of the usual magnitude and characteristics may be expected as a result of changes in growing conditions, location, fertilization, pruning, pest control, and horticultural management practices.

The invention claimed is:

1. A new variety of apple tree denominated SPINK 754, and parts thereof, substantially as illustrated and described.

* * * * *

SPINK 754

CRIPPS PINK ROSY GLOW